United States Patent [19]

Linn et al.

[11] Patent Number: 4,515,783

[45] Date of Patent: May 7, 1985

[54] 4-AMINO-4-DEHYDROXY DERIVATIVES OF EFROTOMYCIN AND RELATED COMPOUNDS

[75] Inventors: Bruce O. Linn, Bridgewater; Aino Lusi, Rahway, both of N.J.

[73] Assignee: Merck & Co., Inc., Rahway, N.J.

[21] Appl. No.: 544,350

[22] Filed: Oct. 24, 1983

[51] Int. Cl.$^3$ .......................... A61K 31/71; C07H 3/06
[52] U.S. Cl. ..................... 514/27; 536/16.8; 536/18.1
[58] Field of Search ............... 424/180, 181; 536/16.8, 536/18.1

[56] References Cited

U.S. PATENT DOCUMENTS 4,024,251  5/1977  Maiese et al. ..................... 424/181

OTHER PUBLICATIONS

Maehr et al., *Canadian Journal of Chemistry,* 58, p. 501 (1980).
Thien-Schranner et al., *Journal of Antibiotics,* XXXV, p. 948 (1982).
Wax et al., "Chem. Abst.", vol. 85, 1976, p. 92146(h).

*Primary Examiner*—Johnnie R. Brown
*Attorney, Agent, or Firm*—David L. Rose; Mario A. Monaco

[57] ABSTRACT

Compounds of the efrotomycin class having a 4-hydroxy-2-pyridone terminal group are converted into 4-amino-4-dehydroxy compounds. The amino group may be substituted with various substituents. The processes for the preparation of such compounds are also disclosed. The amino derivatives have antimicrobial, and growth promotion properties and compositions for such uses are also disclosed.

20 Claims, No Drawings

4-AMINO-4-DEHYDROXY DERIVATIVES OF EFROTOMYCIN AND RELATED COMPOUNDS

BACKGROUND OF THE INVENTION

Efrotomycin is an antibiotic isolated from the fermentation broth of Streptomyces lactamdurans and is disclosed in U.S. Pat. No. 4,024,251. Other antibiotics of related structure are also disclosed such as mocimycin, dihydromocimycin, aurodox, heneicomycin, kirrothricin and the like. The compounds are realized in the following formula:

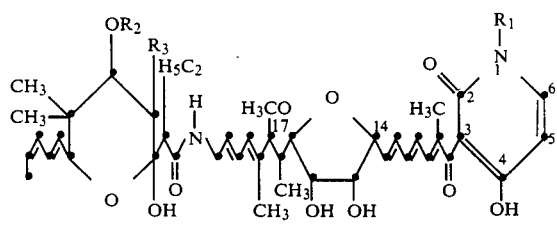

For efrotomycin $R_1$ is methyl, $R_3$ is hydroxy and $R_2$ is:

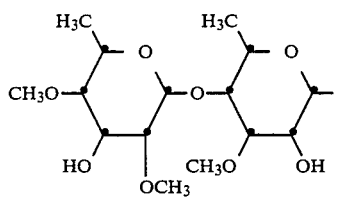

For mocimycin $R_1$ and $R_2$ are hydrogen and $R_3$ is hydroxy; for dihydromocimycin the 5,6-double bond is reduced; for aurodox $R_1$ is methyl, $R_2$ is hydrogen and $R_3$ is hydroxy; for heneicomycin $R_1$ is methyl, $R_2$ and $R_3$ are hydrogen; and for kirrothricin $R_1$ is methyl, $R_2$ and $R_3$ are hydrogen and the furan ring at the 14–17 positions is replaced by

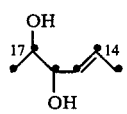

All the compounds have antimicrobial and growth promotion activity. See "The Chemistry of Aurodox and Related Antibiotics." by Maehr et al. in Canadian Journal of Chemistry 58, page 501 (1980). Since Maehr et al. has the structure of kirrothricin listed incorrectly, reference is made to "Metabolic Products of Microorganisms, Kirrothricin," by Thien-Schranner et al., in the Journal of Antibiotics XXXV, page 948, (1982).

SUMMARY OF THE INVENTION

The instant invention is concerned with 4-amino and substituted amino 4-dehydroxy derivative of efrotomycin and related compounds. Thus, it is an object of this invention to describe such compounds. It is a further object to describe processes for the preparation of such compounds. A still further object is to describe the antimicrobial, and growth promotion activity of such compounds. Further objects will become apparent from a reading of the following description.

DESCRIPTION OF THE INVENTION

The 4-amino and substituted amino 4-dehydroxy derivatives of efrotomycin and related compounds have the following structural formula:

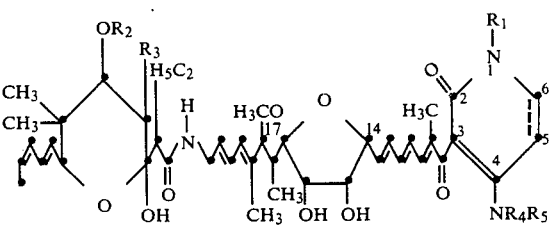

wherein the broken line, $R_1$, $R_2$ and $R_3$ have the following combinations of substituents.

(a) The broken line represents a double bond, $R_1$ is methyl, $R_3$ is hydroxy and $R_2$ is:

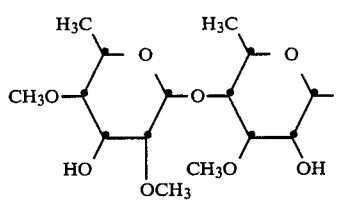

(b) The broken line represents a double bond, $R_1$ and $R_2$ are hydrogen and $R_3$ is hydroxy.

(c) The broken line represents a single bond, $R_1$ and $R_2$ are hydrogen and $R_3$ is hydroxy.

(d) The broken line represents a double bond, $R_1$ is methyl, $R_2$ is hydrogen and $R_3$ is hydroxy.

(e) The broken line represents a double bond, $R_1$ is methyl, $R_2$ and $R_3$ are hydrogen.

(f) The broken line represents a single bond, $R_1$ is methyl, $R_2$ and $R_3$ are hydrogen and the furan ring at the 14–17 positions is replaced by

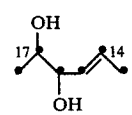

For all of the above groups of compounds $R_4$ and $R_5$ have the following meanings: $R_4$ and $R_5$ are independently hydrogen, loweralkyl, phenyl, phenylloweralkyl, loweralkoxycarbonyl, phenoxycarbonyl, benzyloxycarbonyl, aminocarbonyl, mono- or di(alkylphenyl or phenylalkyl)aminocarbonyl; dialkoxy or diphenoxyphosphinyl; substituted phenylloweralkyl, substituted loweralkyl wherein the substituent is hydroxy, loweralkoxy, loweralkylthio, loweralkylsulfinyl, loweralkylsulfonyl, cyano, mono- or dimethylamino, carbamoyl, carboxy or loweralkoxycarbonyl; or $R_4$ and $R_5$ may be connected to form a heterocyclic ring of 3 to 6 members optionally substituted with hydroxy, carbonyl, loweralkoxy, loweralkylthio, loweralkylsulfonyl, loweralkylsulfinyl or mono- or diloweralkylamino; and optionally the heterocycle may contain a second heteroatom of oxygen, nitrogen or methyl substituted nitrogen.

Compounds of this invention are antibiotics which are effective against both gram-positive and gram-negative bacteria, and accordingly may be used in the treatment of a broad spectrum of infections in animals. More particularly, the compounds are effective against PPLO in chickens, pigs and cattle. It is efficacious subcutaneously against *M. galisepticum*, air sacculitis in broilers and also effective in mice in systemic infections produced by *Bordetella bronchiseptica*. Furthermore, the compounds can be used as growth promoting agents for animals such as chickens, pigs and cattle.

When used in this description of the invention, the term "loweralkyl" is intended to include those alkyl groups of from 1 to 5 carbon atoms such as methyl, ethyl, propyl, iso-propyl, butyl, sec-butyl, tert-butyl, amyl and the like.

The term "loweralkoxy" is intended to include those alkoxy groups of 1 to 5 carbon atoms such as methoxy, ethoxy, propoxy, iso-propoxy, sec-butoxy, tert-butoxy, amyloxy and the like.

The term "carbamoyl" denotes the

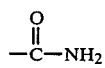

group.

The preferred compounds of this invention are realized in the above formula where, for the compounds a–f, $R_4$ and $R_5$ are independently hydrogen, loweralkyl, hydroxyloweralkyl, diloweralkylaminoalkyl, loweralkoxyalkyl; or $R_4$ and $R_5$ together form a morpholino, piperidino, hydroxypiperidino, aziridinyl or N-methylpiperazinyl group.

The most preferred $R_4$ and $R_5$ substituents are hydrogen, methyl, dimethyl, hydroxyethyl, bishydroxyethyl, dimethylaminoethyl, dimethoxyethyl, N-(dimethylaminoethyl)-N-methyl; or $R_4$ and $R_5$ taken together form a morpholino, piperidinyl, 4-hydroxypiperidinyl, aziridinyl or N-methylpiperazinyl group.

The most preferred of the compounds a–f is efrotomycin (a).

Examples of the most preferred compounds of this invention are as follows:
4-Dimethylamino-4-dehydroxy efrotomycin
4-Dimethylaminoethylamino-4-dehydroxy efrotomycin
4-(2,2-Dimethoxyethyl-1-yl)amino-4-dehydroxyefrotomycin
4-[(N-Dimethylaminoethyl)-N-methyl]amino-4-dehydroxy efrotomycin
4-Hydroxyethylamino-4-dehydroxy efrotomycin
4-Bis(hydroxyethyl)amino-4-dehydroxy efrotomycin
4-(Morpholin-1-yl)-4-dehydroxy efrotomycin
4-(Piperidin-1-yl)-4-dehydroxy efrotomycin
4-(Piperidin-4ol-1-yl)-4-dehydroxy efrotomycin
4-(N-Methyl piperazin-1-yl)-4-dehydroxy efrotomycin
4-(Aziridin-1-yl)-4-dehydroxy efrotomycin
4-Methylamino-4-dehydroxy efrotomycin The instant compounds are prepared by first preparing the alkali metal salt of the compounds a–f, all of hich have a hydroxy group in place of the $NR_4R_5$-group of the compounds of the instant invention. The alkali metal salt is reacted with a substituted chlorophosphate to form a phosphate derivative and the reaction of this phosphate intermediate with an $HNR_4R_5$ compound where such compounds are sufficiently basic to displace the phosphate group. The compounds which generally are not basic enough to displace the phosphate are those wherein $R_4$ and $R_5$ contain a carbonyl bonded to the nitrogen or a phosphate group. The final products containing such group are prepared from the phosphate displacement reaction products which have at least one of $R_4$ and $R_5$ as hydrogen by reacting with an activated form of the carbonyl-containing or phosphate compound.

A different phosphate intermediate is employed depending on whether ammonia or a substituted amine is to be reacted therewith. The reaction is outlined in the following reaction scheme which uses the partial structural formula showing on the pyridone portion of the molecule. The remainder of the molecule is as set forth above.

REACTION SCHEME

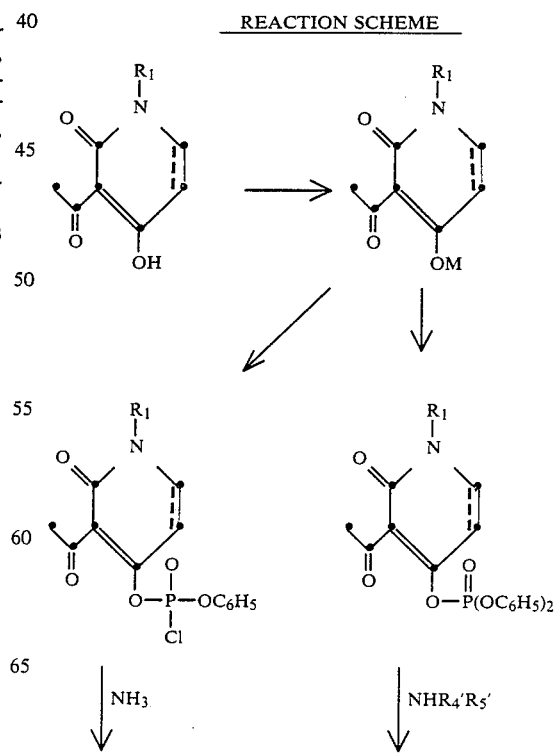

-continued
REACTION SCHEME

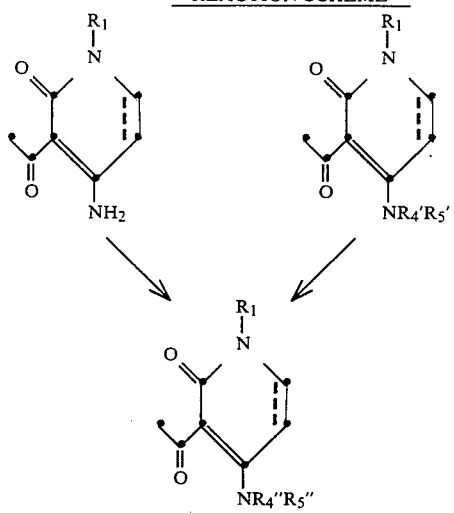

wherein $R_4'$ and $R_5'$ are the groups within the definition of $R_4$ and $R_5$ without the inclusion of phosphate groups and those groups with a carbonyl bonded to the nitrogen; and $R_4''$ and $R_5''$ are those groups within the definition of $R_4$ and $R_5$ with a phosphate or a carbonyl bonded to the nitrogen.

In the first step of the reaction scheme, efrotomycin or efrotomycin-type compound is converted to the alkali metal (M) salt, preferably the sodium salt. The react is carried out in a solvent such as an alchohol, for example, methanol or ethanol using the corresponding alkali metal alkoxide as the reagent. The reaction is carried out at room temperature and is generally complete in from 1 to 5 hours. One equivalent of the alkali metal alkoxide is employed.

The alkali metal salt is then reacted with phenyldichlorophosphate or diphenylchlorophosphate to prepare the appropriate phosphate derivative. The reaction is carried out in a solvent inert to the reaction, such as N,N-dimethylformamide, 1-methyl-2-pyrrolidinone and the like. The reaction is preferably carried out at room temperature although temperatures of from 20° to 50° C. are successful. The reaction is generally complete in from 8 to 18 hours at 25° C.

The phenyldichlorophosphate reactant is employed when the displacement is to be with ammonia since ammonia is a poor nucleophile and the chlorophosphate intermediate provides better results. For other amine reactants the diphenylchlorophosphate is used to prepared the diphenylphosphate intermediate.

The displacement reaction is carried out without isolation of the chlorophosphate intermediate by adding the ammonia gas in excess to the chlorophosphate reaction mixture. For other amination reactions, the phosphate intermediate is generally isolated, purified and then treated with an excess of amine reactant, neat or in solution; up to 20 equivalents of the amine are employed. The reaction mixture is generally stirred at from 20°–80° C. for from 1–100 hours although reaction at room temperature for from 2–20 hours is usually adequate. The mean product is isolated using known techniques. The phosphate displacement reaction is only used for the reactants of sufficient basicity to displace such phosphate groups.

Those reactants with a carbonyl group adjacent to the nitrogen (amides) and phosphates are not sufficiently basic so as to displace the phosphate. To prepare such compounds the compound where at least one of $R_4$ and $R_5$ is hydrogen is reacted with an activated form of the amide or phosphate. Generally an acid chloride or a chlorophosphate are employed. The reaction is carried out in the presence of a base to react with the liberated hydrogen chloride. Tertiary amines, such as pyridine, triethylamine or diisopropylethylamine are acceptable. The reaction is carried out in a solvent such as methylene chloride, chloroform, diethylether, tetrahydrofuran, and the like. Reactions with one equivalent of an acid chloride are preferably carried out at 0° to 5° C. and take 1 to 14 days. Reactions with two equivalents of acid chloride or with one equivalent of chlorophosphate are generally run at 20° to 25° C. and take 20 to 48 hours.

The instant compounds show activity against gram-negative and gram-positive bacteria and species of Mycoplasma. In vitro, the instant compounds are effective against *E. acervulina*, Bordetella, *Streptococcus faecalis*, *Streptococcus faecum*, *Streptococcus agalactiae*, *Streptococcus pyogenes*, *Proteus vulgaris*, *M. hyorhinis*, *M. synoviae*, *M. arthritidis*, *M. gallisepticum* and species of Pasteurella. Activity was also found against *Vibrio percolans* (ATCC 8461), *Salmonella gallinarum* (MB 1287), *E. coli* (MB 1418), *Klebsiella pneumoniae* (MB 1264), *Pseudomonas stutzeri* (MB 1231) and (MB 2765), *Bacillus subtilis* (MB 964) and (MB 797), *Staphylococcus aureus* (MB 108), (MB 210) and (MB 703), and *Psuedomonas aeruginosa* (MB 3210).

The instant compounds are useful both as antibiotics and as growth promoting agents in animals.

When the instant compounds are used as antibiotic, the specific means employed for administering it to the animal is not critical and any of the methods now used or available for treating infected animals or animals susceptible to infection are satisfactory.

The instant compounds can be used as antibiotics, for example, in the form of pharmaceutical preparations which contain them in admixture or conjunction with an organic or inorganic, solid or liquid pharmaceutical excipient suitable for enteral, parenteral or local administration. Suitable excipients are substances that do not react with the antibiotic, for example, water, gelatin, lactose, starches, steryl alcohol, magnesium stearate, talcum, vegetable oils, benzyl alcohols, gums, propyleneglycol, polyalkyleneglycols, white petroleum jelly, cholesterol or other known medicinal esecipients. The pharmaceutical preparations may be, for example, tablets, dragees, ointments, creams or capsules, or in liquid form solutions, suspensions or emulsions. They may be sterilized and/or contain assistants, such as preserving, stabilizing, wetting or emulsifying agents; solution promoters, salts for regulating the osmotic pressure or buffers.

Where it is desired to administer the antibiotic in dry, solid unit dosge form, capsules, boluses or tablets containing the desired amount of antibiotic are employed. These dosage forms are prepared by intimately and unformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the instant compounds depending upon factors such as the type of host animal to be treated, the severity and type of infection and the weight of the host. The antibiotic may be administered on a daily basis at from about 5 to 100 mg perkilograms of body weight.

Included in this invention are the nontoxic, pharmaceutically acceptable salts of the instant compounds, for example, the mineral acid addition salts such as hydrochloride, hydrobromide, sulfate, phosphate, nitrate and the like or the organic addition salts such as acetate, citrate, pyruvate, tartarate and the like.

In addition to its use as an antibiotic, the instant compounds are useful as feed additives to promote the growth of animals such as chickens, sheep and cattle. The use of the instant compounds shortens the time required fo bringing animals up to marketable weight.

When the instant compounds are used as growth promoters in animals, they can be administered as components of the feed of the animals or may be dissolved or suspended in the drinking water.

When the instant compounds are used as components of animal feed, they are first formulated as feed supplement. In such feed supplements, the instant compounds are present in relatively concentrated amounts intimately dispersed in an inert carrier or diluent. The feed supplement can be added directly to the feed or made into a premix by an intermediate dilution or blending step. By inert carrier is meant one that will not react with the antibiotic and one that may be administered safely to animals. Preferably, the carrier is one that is or may be, and ingredient of the animal ration. Typical carriers or diluents suitable for such composition include, for example, distillers' dried grains, corn meal, citrus meal, fermentation residues, ground oyster shells, wheat shorts, molasses solubles, corn cob meal, edible beam mill feed, soya grits, crushed limestone and the like. The antibiotic is intimately dispersed throughout the carrier by methods such as grinding, stirring, milling or tumbling. Compositions containing from about 5 to 50% by weight of the antibiotic are particularly suitable as feed supplements.

Examples of typical feed supplements containing the instant compounds dispersed in a solid carrier are:

|     |                          | lbs. |
| --- | ------------------------ | ---- |
| (A) |                          | 5    |
|     | Wheat Standard Middling  | 95   |
| (B) |                          | 50   |
|     | Corn distiller's grains  | 50   |

These and similar feed supplements are prepared by uniformly mixing the antibiotic with the carrier.

The feed supplement can be added directly to the feed or made into a premix by an intermediate dilution or blending step with an orally ingestible carrier. Compositions containing 0.03% to 5% by weight of the antibiotic are particularly suitable as premixes. These premixes are prepared by uniformly mixing the antibiotic with an orally ingestible carrier.

Such supplements or premixes are added to the animal feed in an amount to give the finished feed the concentration of the instant compounds desired for growth promotion. In chickens, the instant compounds are fed at a final concentration of between 50 gm to 300 gm per ton of feed in order to achieve the desired growth promoting result. In the case of swine, including swine infected with *M. hyorhinis*, the instant compounds may be administered in the feed at similar levels.

In the above discussion of this invention, emphasis has been placed on solid compositions wherein the instant compounds are mixed with an edible carrier in a feed supplement, in a so-called premix or in the final feedstuff. This is the preferred method of administering the instant compounds. An alternate method is to dissolve or suspend the instant compounds in the drinking water of the animals. The quantity that may be suspended in the water without undue settling is limited. Emulsifiers or surface-active agents may be employed for this latter purpose.

It will likewise be understood by those skilled in this art that special feed supplement formulations and finished animal feeds containing the instant compounds may also include vitamins, other antibiotics and growth-promoting agents and other nutritional substances.

The instant compounds are useful against poultry PPLO at a range of 5 to 100 mg/kg. A preferred range for a single dose is from 35 to 45 mg/kg. For reasons of convenience a preferred method of administering the antibiotic in the treatment of PPLO is to admix the instant compounds with the animal feed. A preferred range for PPLO is from 0.0055% to 0.2% by weight of feed.

In the treatment of air sacculitis in broilers the $ED_{50}$ is 40 to 100 mg/kg. Accordingly, a useful dosage of the instant compounds may vary from 10 to 150 mg/kg.

A solution or suspension for subcutaneous injection for treatment of air sacculitis in broilers may be prepared as follows:

Subcutaneous Solution or Suspension Containing 20 mg of the Instant Compounds Ampoule:

|                                     | 20 mg |
| ----------------------------------- | ----- |
| Diluent: Sterile water for injection | 2 cc  |

In the treatment of the preferred method of administering the instant compounds is in the feed at a level of from about 0.5 to 2% by weight of feed.

It will be appreciated that the dosage to be administered depends to a large extent upon the condition and weight of the host; the parenteral route is preferred for air sacculitis and the oral route is preferred for PPLO. The preferred route of administering the instant compounds for growth promotion is by admixing in feed.

The examples which follow illustrate methods by which the product of this invention may be obtained. The claimed process is capable of wide variation and modification and, therefore, any minor departure therefrom or extension thereof is considered as being within the skill of the artisan and as falling within the scope of this invention.

EXAMPLE 1

Efrotomycin (FR-02A)

A crude preparation of efrotomycin (FR-02A) was isolated from *Streptomyces lactamdurans* NRRL 3802 as described in U.S. Pat. No. 4,024,251 and *The J. Antibiotics* 24 (6) 670, 1976 (R. Wax, W. Maiese, R. Weston and J. Birnbaum). The major component is efrotomycin (FR-02A) and is further purified by column chromatography. Crude efrotomycin (FR-02A), 95 g, was dissolved in 950 ml of $CH_2Cl_2$-$CH_3OH$ 95:5 was treated with 42 g of a filter aid—diatomaceous earth. The suspension was filtered and the filtrate evaporated to dryness in vacuo with brief warming to 45° C. The residue was redissolved in 300 ml of the same solvent and was percolated through a column, 7.0 cm ID × 80 cm long, containing 1.2 kg of E. Merck silica gel 60. The column was eluted with the same solvent. Fractions were inspected by TLC on Analtech silica gel GF using two solvent systems: methylene chloride-methanol-water 90:10:0.1 and methylene chloride-methanol-concentrated ammonium hydroxide 90:10:0.1. The appropriate fractions were combined and evaporated furnishing efrotomycin as an amorphous yellow powder; UV methanolic 0.01 N HCl λmax 230 nm, ($\epsilon$65,900), 327 nm, ($\epsilon$36,400); UV in methanolic 0.01 N NaOH λmax 223 nm, ($\epsilon$70,200), 319 nm, ($\epsilon$36,200); certain characteristic proton NMR signals (CDCl$_3$, 300 MHz)δ3.46 (s, pyridone NCH$_3$), 5.99 (d, J=8.0 Hz, C$_5$H), 7.40 (d, J=8.0 Hz, C$_6$H); laser field desorption mass spectrum, m/e 1145 (M+H)$^+$.

Anal. Calc'd for $C_{59}H_{88}N_2O_6 \cdot H_2O$ (1163.4): C, 60.91; H, 7.81; N, 2.41; LOD (H$_2$O) 1.6. Found: C, 60.82; H, 7.76; N, 2.64; LOD (H$_2$O) 1.8.

EXAMPLE 2

Efrotomycin (FR-02A)-4-O-sodium

Purified efrotomycin (FR-02A), 40.0 g (35 mmol) was dissolved in 350 ml of dry methanol and cooled to about 5° C. in an ice water bath. A solution containing one equivalent of sodium methoxide, 1.89 g (35.0 mmol) in 30 ml of dry methanol was added dropwise with stirring under a nitrogen atmosphere until a pH of 8.6 was obtained as measured by diluting a small aliquot with 4 portions of H$_2$O. After the addition was completed, the ice water bath was removed and the solution stirred at room temperature, 23° C., for 3.5 hours. The solution was concentrated in vacuo on a rotary evaporator with warming to 30° C. The resulting powder was further dried by pumping in high vacuum overnight at room temperature, 23°C., furnishing 39.1 g of efrotomycin (FR-02A)-4-O-sodium. The structure was confirmed by ultraviolet, proton nuclear magnetic resonance, LFD mass spectral and elemental analysis:

UV methanolic 0.01 N HCl λmax 230 nm, ($\epsilon$67,000), 325 nm, ($\epsilon$36,900); UV methanolic 0.01 N NaOH λmax 221 nm, ($\epsilon$71,000), 317 nm, ($\epsilon$36,100); distinguishing $^1$H NMR signals (Me$_2$SO-d$_6$, 300 M Hz) δ3.10 (s. pyridone NCH$_3$), 5.28 (d, J=8.0 Hz, C$_5$-H), 7.02 (d, J=8.0 Hz, C$_6$-H).

Anal. Calc'd for $C_{59}H_{87}N_2O_{20}Na \cdot 2H_2O$; C, 58.89; H, 7.62; N, 2.33; Na, 1.91; LOD (H$_2$O) 2.1. Found: C, 58.73; H, 7.83; N, 2.11; Na, 1.95; LOD 2.6.

EXAMPLE 3

Efrotomycin (FR-02A)-4-O-phenylchlorophosphate

Phenyldichlorophosphate, 450 μl (3.00 mmol) was added dropwise over several minutes with stirring to a solution of efrotomycin (FR-02A)-4-O-sodium, 3.60 g (3.00 mmol), in 15 ml of dimethylformamide under a nitrogen atmosphere. Stirring was continued for 8 hours at room temperature, 23° C. The progress of the reaction was followed by TLC on silica gel GF 10 cm plates using methylene chloride-methanol-concentrated ammonium hydroxide 95:5:0.5. The reactive efrotomycin (FR-02A)-4-O-phenylchlorophosphate was obtained in solution and used in situ for reaction with ammonia and amines.

EXAMPLE 4

4-Amino-4-dehydroxy Efrotomycin (FR-02A)

The solution containing 3.0 mmol of efrotomycin (FR-02A)-4-O-phenylchlorophosphate in 15 ml of dimethylformamide for Example 2 was treated with excess ammonia gas. The ammonia bubbled into the solution at a rapid rate for about 30 seconds. Stirring was continued at room temperature, 23° C., for 16 hours. The progress of the reaction was monitored by TLC on silica gel GF 10 cm plates using methylene chloride-methanol-water 95:5:0.5. The reaction solution was diluted with methylene chloride and extracted twice with dilute aqueous sodium bicarbonate. The organic phase was dried over anhydrous sodium sulfate and evaporated in vacuo with brief warming (<45° C.) leaving 5.10 g. of residue. The residue was chromatographed on a column of silica gel 60, 140 g, using methylene chloride-methanol-water 95:5:0.5 furnishing 1.79 g of 4-amino-dehydroxy efrotomycin FR-02A as an amorphous powder. The structure was determined by proton nuclear resonance, ultraviolet, LFD mass spectral and elemental analyses: UV methanolic 0.1 NHCl λmax 230 nm ($\epsilon$62,500) 270 nm ($\epsilon$30,000) 292 nm ($\epsilon$27,200) 354 nm ($\epsilon$22,500); distinguishing $^1$HNMR signals (CDCl$_3$, 300 MHz) J 3.08 (d, J=4.5 Hz, NCH$_3$Hz, NCH$_3$) 3.29 (s, pyridone NCH$_3$) 5.76 (d, J=8.0 Hz, C$_5$H) 7.07 (d, J=8.0 Hz, C$_6$H); LFD mass spectrum, m/e 1144 (M+H)$^+$.

Analysis calculated for $C_{59}H_{89}N_3O_{19} \cdot H_2O$: C, 61.93; H, 7.84; N, 3.67; LOD (H$_2$O) 1.57. Found: C, 61.57; H, 7.94; N, 3.64; LOD 2.0.

EXAMPLE 5

Efrotomycin (FR-02A)-4-O-diphenylphosphate

Diphenyl chlorophosphate, 2.64 ml (12.0 mmol) was added dropwise to a stirred solution of efrotomycin (FR-02A)-4-O-sodium, 14.0 g (12.0 mmol) in 60 ml of dry dimethylformamide under nitrogen at ambient temperature. The mixture was stirred at room temperature, 23° C., until the reaction was complete (about 18 hours, as determined by TLC on silica gel GF plate using methylene chloride-methanol 95:5). The reaction mixture was then taken up in methylene chloride and extracted with five portions of cold aqueous sodium bicarbonate followed by one portion of aqueous sodium chloride. The methylene chloride solution was dried over anhydrous sodium sulfate and then evaporated in vacuo with brief water bath warming to 45° C. leaving 22.0 g of a glass residue. The residue was chromatographed on a column of silica gel 60, 240 g, methylene chloride-methanol 95:5 as eluant which furnished 13.85 g of efrotomycin (FR-02A)-4-O-diphenylphosphate as an amorphous powder. The structure was confirmed by proton nuclear magnetic resonance, ultraviolet, LFD mass spectral and elemental analyses:

UV in methanol λmax 229 nm, ($\epsilon$62,200), 332 nm, ($\epsilon$37,500); distinguishing $^1$H NMR signals (CDCl$_3$, 300 MHz) δ3.55 (s, pyridone NCH$_3$), 6.60 (d, J=8.0 Hz, C$_5$H), 6.68 (m, C$_9$H), 7.16, 7.19, 7.24, 7.26, 7.33, 7.35, 7.38 (m, OC$_6$H$_5$+C$_6$H); LFD mass spectrum, m/e 1399 (M+Na)$^+$, 482 [(C$_6$H$_5$O)$_2$PO]$_2$O, 250 [(C$_6$H$_5$O)$_2$PO$_2$H].

Anal. Calc'd for $C_{71}H_{97}O_{23}P$: C, 61.91; H, 7.10; N, 2.03; P, 2.25. Found: C, 61.63; H, 7.34; N, 1.89; P, 2.03.

EXAMPLE 6

4-Dimethylamino-4-dehydroxy Efrotomycin (FR-02A)

An excess quantity of dimethylamine gas was bubbled for about 60 seconds into a stirred solution of efrotomycin (FR-02A)-4-O-diphenylphosphate, 2.0 g, in 2.0 ml of dry dimethylformamide under nitrogen at room temperature, 22° C. Stirring was continued at 22° C. until the reaction was complete, (about 20 hours, as determined by TLC on silica gel GF 10 cm plates using methylene chloride-methanol-water 95:5:0.5). The reaction solution was diluted with methylene chloride and extracted twice with aqueous sodium bicarbonate and once with aqueous sodium bicarbonate. The organic phase was dried over anhydrous sodium sulfate and evaporated in vacuo with brief warming below 45° C. leaving 2.15 g of a viscous residue. The residue was chromatographed on a column of silica gel 60, 90 g, using methylene chloride-methanol 95:5 furnishing 868 mg of 4-dimethylamino-4-dehydroxy efrotomycin (FR-02A) as an amorphous powder. The structure was confirmed by proton nuclear magnetic resonance, ultraviolet, LFD mass spectral and elemental analyses:

UV in methanolic 0.01 N HCl λmax 233 nm (ε73,000), 328 nm (ε33,100); distinguishing $^1$H NMR signals (CDCl$_3$, 300 MHz) ε2.87 (s, N(CH$_3$)$_2$), 3.39 (s, pyridone NCH$_3$), 5.87 (d, J=8.0 Hz, C$_5$H), 7.00 (d, J=11.0 Hz, C$_9$H), 7.09 (d, J=8.0 Hz, C$_6$H); LFD mass spectrum, m/e 1172 (m H)$^+$.

Anal. Calc'd for C$_{61}$H$_{93}$N$_3$O$_{19}$: C, 62.49; H, 8.00; N, 3.58. Found: C, 62.66; H, 7.98; N, 3.74.

EXAMPLE 7

4-morpholin-1-yl-4-dehydroxy Efrotomycin (FR-02A)

A solution containing 1.38 g (1.0 mmol) of efrotomycin (FR-02A)-4-O-diphenylphosphate and 0.52 ml (6.0 mmol) of dry morpholine in 5.0 ml of dry dimethylformamide was stirred at 23° C., room temperature under nitrogen for 24 hours. The reaction was followed by TLC inspection on Analtech silica gel GF 10 cm plates using methylene chloride-methanol-concentrated ammonium hydroxide 90:10:1.0. The reaction solution was diluted with methylene chloride and then extracted with 4 portions of chilled water and 4 portions of chilled dilute aqueous sodium bicarbonate. The methylene chloride solution was dried over anhydrous sodium sulfate and concentrated in vacuo with water bath warming below 45° C. leaving 1.22 g of crude product as a foam solid. The product was purified by chromatography on a column of E. Merck silica gel 60, 60 g, using methylene chloride-methanol-concentrated ammonium hydroxide 95:5:0.5 as eluant furnishing 581 mg of 4-(4-morpholinyl)-4-dehydroxy efrotomycin (FR-02A) as an amorphous powder. The product was identified by proton nuclear magnetic resonance, mass spectral and elemental analyses.

EXAMPLE 8

4-Dimethylaminoethylamino-4-dehydroxy Efrotomycin (FR-02A)

A solution containing 1.38 g (1.0 mmol) of efrotomycin-4-O-diphenylphosphate and 1.1 m (10 mmol) of dry unsym. dimethylethylene diamine in 4.0 ml of dry dimethylformamide was stirred at 23° C., room temperature, for 26 hours. Completion of the reaction was determined by TLC on silica gel GF 10 cm plates using methylene chloride-methanol-H$_2$O 90:10:1. The reaction solution was diluted with methylene chloride and extracted with 2 portions of chilled aqueous sodium bicarbonate and 1 portion of saturated aqueous sodium chloride. The methylene chloride solution was dried over anhydrous sodium sulfate and then evaporated in vacuo with water bath warming below 45° C. leaving the crude product as a foam solid. The crude product was purified by column chromatography on silica gel 60, 32 g, using methylene chloride-methanol 95:5 as eluant providing 687 mg of 4-dimethylaminoethylamino-4-dehydroxy efrotomycin (FR-02A) as an amorphous powder. The product was characterized by proton nuclear resonance, mass spectral and elemental analyses.

EXAMPLE 9

4-Methoxycarbonylamino-4-dehydroxy Efrotomycin (FR-02A)

Methyl chloroformate, 8.5 μl (0.11 mmol) was added with stirring to an ice bath chilled solution containing 115 mg (0.10 mmol) of 4-amino-4-dehydroxy efrotomycin (FR-02A), 58 μl (0.33 mmol) of diisopropylethylamine and 18 μl (0.22 mmol) of pyridine in 2.0 ml of dry methylene chloride. The reaction was monitored by TLC on silica gel GF 10 cm plates using methylene chloride-methanol-water 90:10:1. The solution was stirred at 5° C. for 4 days and then it was diluted wtih methylene chloride and extracted twice with chilled aqueous 5% potassium phosphate monobasic (pH 4.4), twice with chilled aqueous sodium bicarbonate and once with saturated aqueous sodium chloride. The organic phase was dried over anhydrous sodium sulfate and then evaporated in vacuo with water bath warming below 45° C. leaving the crude product as a glass solid. The product was purified by chromatography on a column of silica gel 60, 10 g, using methylene chloride-methanol 95:5 furnishing 19 mg of 4-methoxycarbonylamino-4-dehydroxy efrotomycin (FR-02A) as an amorphous solid. The structure was determined by proton nuclear magnetic resonance, LFD mass spectral and elemental analyses.

EXAMPLE 10

4-Bis(Ethocycarbonyl)amino-4-dehydroxy Efrotomycin (FR-02A)

The procedure of Example 9 was followed using 21 μl (0.22 mmol) of ethyl chloroformate. After the addition was completed, the ice bath was removed and the reaction solution was stirred at 23° C., room temperature, for 48 hours. 4-Bis(ethoxycarbonyl)amino-4-dehydroxy efrotomycin (FR-02A), 35 mg, was obtained as an amorphous powder which was identified by proton nuclear magnetic resonance, LFD mass spectral and elemental analyses.

EXAMPLE 11

4-Dimethylaminocarbonylamino-4-dehydroxy Efrotomycin (FR-02A)

The procedure of Example 9 was repeated using 11.1 μl (0.12 mmol) of dimethylcarbamyl chloride. The reaction solution was stirred at 5° C. for 14 days. 4-Dimethylaminocarbonylamino-4-dehydroxy efrotomycin (FR-02A) 70 mg was obtained as an amorphous powder which is identified by proton nuclear magnetic resonance and elemental analyses.

EXAMPLE 2

4-Diphenoxyphosphinylamino-4-dehydroxy Efrotomycin (FR-02A)

The procedure of Example 9 was followed using 22.7 μl (0.11 mmol) of diphenylchlorophosphate. The reaction solution was stirred 21 hours at 5° C. and then 20 hours at 23° C., room temperature. 4-Diphenoxyphosphinylamino-4-dehydroxy efrotomycin (FR-02A), 14.2 mg, was obtained as an amorphous solid which was characterized by proton nuclear magnetic resonance and LFD mass spectral analyses.

EXAMPLE 13

4-Acetylamino-4-dehydroxy Efrotomycin (FR-02A)

The procedure of Example 9 is followed using 8.5 μl (0.12 mmol) of acetyl chloride. 4-Acetylamino-4-dehydro efrotomycin (FR-02A) is obtained.

TABLE I

4-Amino- and 4-Substituted Amino-4-dehydroxy Efrotomycins Substituted With Hydrocarbons Prepared by Amine Displacement of the Phosphate Intermediates as in Examples 4, 6 and 7

| Amine Reactant | Efrotomycin Product 4-Substituent | Identification |
|---|---|---|
| Ammonia | 4-Amino | A, B, C, D |
| Methylamine | 4-Methylamino | A, B, C, D |
| Dimethylamine | 4-Dimethylamino | A, B, C, D |
| Ethylamine | 4-Ethylamino | |
| N—Ethylmethylamine | 4-(N—Ethyl-N—methyl)-amino | |
| Diethylamino | 4-Diethylamino | |
| Isopropylamino | 4-Isopropylamino | A, B, C, D |
| n-Butylamine | 4-n-Butylamino | A, B, C |
| Tridecylamine | 4-Tridecylamino | A, B, C |
| Cyclohexylamine | 4-Cyclohexylamino | A, B, C |
| Cyclopropylamine | 4-Cyclopropylamino | |
| Benzylamine | 4-Benzylamino | A, B, C |
| Phenethylamine | 4-Phenethylamino | A, B, C |

A Proton nuclear magnetic resonance
B Elemental analysis; C, H and N
C Thin layer chromatography
D LFD mass spectral analysis

TABLE II

4-Substituted-4-dehydroxy Efrotomycins Substituted with Heterocyclic Amines Prepared by Amine Displacement of the 4-Phosphate Intermediates as in Examples 7 and 8

| Heterocyclic Amine Reagent | Efrotomycin Product 4-Substituent | Identification |
|---|---|---|
| Piperidine | 4-(Piperidin-1-yl) | A, B, C, D |
| Pyrrolidine | 4-(Pyrrolidin-1-yl) | |
| Azetidine | 4-(Azetidin-1-yl) | |
| Ethyleneimine | 4-(Aziridin-1-yl) | |
| 4-Piperidinol | 4-(Piperidin-4-ol-1-yl) | A, B, C, D |
| 4-Piperidone | 4-(Piperidin-4-one-1-yl) | A, C, D |
| Morpholine | 4-(Morpholin-1-yl) | A, B, C |
| N—Methylpiperazine | 4-(4-Methylpiperazin-1-yl) | |
| 3-(1-Piperazinyl)-1,2-propanediol | 4-[4-(3-Propane-1,2-diol)piperazin-1-yl] | A, B, C, D |

A, B, C, D - See footnotes in Table I.

TABLE III

4-Substituted Amino-4-dehydroxy Efrotomycins Substituted with Hydrocarbons Containing Functional Groups Prepared by Amino Displacemeht of the 4-Phosphate Intermediates as in Examples 7 and 8

| Amine Reactant | Efrotomycin Product 4-Substituent | Identification |
|---|---|---|
| Ethanolamine | 4-(2-Hydroxyethyl)amino | A, B, C |
| 3-Amino-1-propanol | 4-(3-Hydroxypropyl)amino | |
| 2-Methoxyethylamine | 4-Methoxyethylamino | A, B, C |
| 2-Methylthioethylamine | 4-Methylthioethylamino | A, B, C |
| unsym. Dimethylethylenediamine | 4-Dimethylaminoethylamino | A, B, C |
| 3-Dimethylaminopropylamine | 4-(3-Dimethylaminopropyl)amino | |
| Diethanolamine | 4-Bis(2-hydroxyethyl)-amino | A, C, D |
| Glycinamide hydrochloride[F] | 4-Carbamylmethylamino | A, B, C, D |
| Aminoacetaldehyde dimethylacetal | 4-(2,2-Dimethoxyeth-1-yl)amino | A, B, C |
| Aminoacetonitrile hydrochloride | 4-Cyanomethylamino | A, B, C |
| 2,4-Dimethoxybenzylamine | 4-(2,4-Dimethoxybenzyl)-amino | A, B, C |
| N—N—Dimethyl-N′—methylethylenediamine | 4-[N—(Dimethylaminoethyl)-N—methyl]amino | |
| 2-Chloroethylamine hydrochloride[F] | 4-(2-Chloroethyl)amino | |

A, B, C, D - See Table I.
[F]The free base is formed in situ by addition of diisopropylethylamine.

TABLE IV

4-Alkanoxy and 4-Phenoxy Carbonylamino-4-dehydroxy Efrotomycins Prepared from the 4-Amino Derivative and the Corresponding Chloroformates as in Example 9

| Chloroformate Reagent | Efrotomycin Product 4-Substituent | Identification |
|---|---|---|
| Methylchloroformate | 4-Methoxycarbonylamino | A, B, C |
| Ethylchloroformate | 4-Ethoxycarbonylamino | A, C, D |
| Butylchloroformate | 4-Butoxycarbonylamino | |
| Tridecylchloroformate | 4-Tridecyloxycarbonylamino | |
| Benzylchloroformate | 4-Benzoxycarbonylamino | |
| Phenylchloroformate | 4-Phenoxycarbonylamino | |

A, B, C, D - See footnotes in Table I.

TABLE V

4-Bis Alkanoxy- and 4-Bis Phenoxycarbonylamino-4-dehydroxy Efrotomycins Prepared from the 4-Amino Derivative and the Corresponding Chloroformates as in Example 10

| Chloroformate Reagent | Efrotomycin Product 4-Substituent | Identification |
|---|---|---|
| Methylchloroformate | 4-Bis(Methoxycarbonyl)-amino | |
| Ethylchloroformate | 4-Bis(Ethoxycarbonyl)amino | A, B, C, D |
| Butylchloroformate | 4-Bis(Butoxycarbonyl)amino | |
| Tridecylchloroformate | 4-Bis(Tridecyloxycarbonyl)amino | |
| Benzylchloroformate | 4-Bis(Benzyloxycarbonyl)amino | |
| Phenylchloroformate | 4-Bis(Phenoxycarbonyl)amino | |

A, B, C, D - See footnotes in Table I.

TABLE VI

4-Substituted Aminocarbonylamino-4-dehydroxy Efrotomycins Substituted with Hydrocarbons Prepared from the 4-Amino Derivative and a Carbamyl Chloride as Example 11

| Carbamyl Chloride Reagent | Efrotomycin Product 4-Substituent | Identification |
|---|---|---|
| Dimethylcarbamyl chloride | 4-Dimethylaminocarbonylamino | A, B, C |
| Ethylmethylcarbamyl chloride | 4-Ethylmethylaminocarbonylamino | |
| Diethylcarbamyl chloride | 4-Diethylaminocarbonylamino | |
| Butylmethylcarbamyl chloride | 4-(N—Butyl-N—methylamino)carbonylamino | |
| Methyltridecylcarbamyl chloride | 4-(N—methyl-N—tridecylamino)carbonylamino | |
| Benzylmethylcarbamyl chloride | 4-(N—Benzyl-N—methylamino)carbonylamino | |
| Methylphenylcarbamyl chloride | 4-(N—Methyl-N—phenylamino)-carbonylamino | |

A, B, C - See footnotes in Table I.

TABLE VII

4-Dialkyloxy and 4-Diphenoxyphosphinylamino-4-dehydroxy Efrotomycins Prepared from the 4-Amino Derivative and the Corresponding Chlorophosphates as in Example 12

| Chlorophosphate Reagent | Efrotomycin Product R-Substituent | Identification |
|---|---|---|
| Diphenylchlorophosphate | 4-Diphenoxyphosphinylamino | A, C, D |
| Dimethylchlorophosphate | 4-Dimethoxyphosphinylamino | |
| Diethylchlorophosphate | 4-Diethoxyphosphinylamino | |
| Dibutylchlorophosphate | 4-Dibutoxyphosphinylamino | |
| Dibenzylchlorophosphate | 4-Dibenzyloxyphosphinylamino | |

A, C, D - See footnotes in Table I.

TABLE VIII

4-Alkanoyl- and 4-Benzoylamino-4-dehydroxy Efrotomycins Prepared from the 4-Amino Derivative and the Corresponding Carboxyl Chlorides as in Example 13

| Carboxyl Chloride Reagent | Efrotomycin Product 4-Substituent | Identification |
|---|---|---|
| Acetyl chloride | 4-Acetylamino | |
| Propionyl chloride | 4-Propionylamino | |
| Butyryl chloride | 4-Butyrylamino | |
| Steroyl chloride | 4-Steroylamino | |
| Benzoyl chloride | 4-Benzoylamino | |

What is claimed is:

1. A compound having the formula:

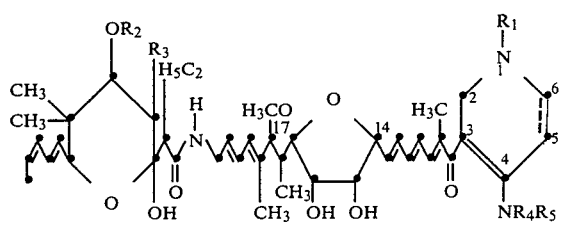

wherein the broken line, $R_1$, $R_2$ and $R_3$ have the following combinations of substituents:

(a) the broken line represents a double bond, $R_1$ is methyl, $R_3$ is hydroxy and $R_2$ is:

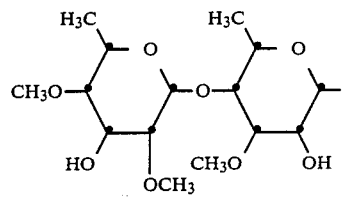

(b) the broken line represents a double bond, $R_1$ and $R_2$ are hydrogen and $R_3$ is hydroxy;

(c) the broken line represents a single bond, $R_1$ and $R_2$ are hydrogen and $R_3$ is hydroxy;

(d) the broken line represents a double bond, $R_1$ is methyl, $R_2$ is hydrogen, and $R_3$ is hydroxy;

(e) the broken line represents a double bond, $R_1$ is methyl, $R_2$ and $R_3$ are hydrogen;

(f) the broken line represents a single bond, $R_1$ is methyl, $R_2$ and $R_3$ are hydrogen and the furan ring at the 14–17 positions is replaced by

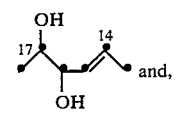 and, for all of the above groups of compounds $R_4$ and $R_5$ have the following meanings: $R_4$ and $R_5$ are independently hydrogen, loweralkyl, phenyl, phenylloweralkyl, loweralkoxycarbonyl, phenoxycarbonyl, benzyloxycarbonyl, aminocarbonyl, mono- or di(alkylphenyl or phenylalkyl)aminocarbonyl; dialkoxy or diphenoxyphosphinyl; substituted phenylloweralkyl, substituted loweralkyl wherein the substituent is hydroxy, loweralkoxy, loweralkylthio, loweralkylsulfinyl, loweralkylsulfonyl, cyano, mono- or dimethylamino, carbamoyl, carboxy or loweralkoxycarbonyl; or $R_4$ and $R_5$ may be connected to form a heterocyclic ring of 3 to 6 members unsubstituted or substituted with hydroxy, carbonyl, loweralkoxy, loweralkylthio, loweralkylsulfonyl, loweralkylsulfinyl or mono- or diloweralkylamino; and the heterocycle may contain a second heteroatom of oxygen, nitrogen or methyl substituted nitrogen.

2. The compound of claim 1 wherein $R_4$ and $R_5$ are independently hydrogen, loweralkyl, hydroxyloweralkyl, diloweralkylaminoalkyl, loweralkoxyalkyl or $R_4$ and $R_5$ together form a morpholino, piperidino, hydroxypiperidino, aziridinyl, or N-methylpiperazinyl group.

3. The compound of claim 2 wherein $R_4$ and $R_5$ are hydrogen, methyl, dimethyl, hydroxyethyl, bis-hydroxyethyl, dimethylaminoethyl, dimethoxyethyl, N-(dimethylaminoethyl)-N-methyl or $R_4$ and $R_5$ taken together form a morpholino, piperidinyl, 4-hydroxypiperidinyl, aziridinyl or N-methylpiperazinyl group.

4. The compound of claim 1 wherein the broken line represents a double bond, $R_1$ is methyl, $R_3$ is hydroxy and $R_2$ is:

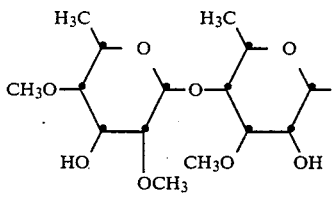

5. The compound of claim 4 which is 4-dimethylamino-4-dehydroxy efrotomycin.

6. The compound of claim 4 which is 4-dimethylaminoethylamino-4-dehydroxy efrotomycin.

7. The compound of claim 4 which is 4-(2,2-dimethoxyethyl-1-yl)amino-4-dehydroxy efrotomycin.

8. The compound of claim 4 which is 4-[(N-dimethylaminoethyl)-N-methyl]amino-4-dehydroxy efrotomycin.

9. The compound of claim 4 which is 4-Hydroxyethylamino-4-dehydroxy efrotomycin.

10. The compound of claim 4 which is 4-bis-(Hydroxyethyl)amino-4-dehydroxy efrotomycin.

11. The compound of claim 4 which is 4-(morpholin-1-yl)-4-dehydroxy efrotomycin.

12. The compound of claim 4 which is 4-(piperidin-1-yl)-4-dehydroxy efrotomycin.

13. The compound of claim 4 which is 4-(piperidin-4-ol-1-yl)-4-dehydroxy efrotomycin.

14. The compound of claim 4 which is 4-(N-methylpiperizin-1-yl)-4-dehydroxy efrotomycin.

15. The compound of claim 4 which is 4-(aziridin-1-yl)-4-dehydroxy efrotomycin.

16. The compound of claim 4 which is 4-methylamino-4-dehydroxy efrotomycin.

17. A method for promoting the growth of ruminant and monogastric animals which comprises administering an effective amount of a compound of claim 1.

18. A method for treating PPLO infections which comprises administering to an animal so infected an effective amount of a compound of claim 1.

19. A composition useful for administration to animals for promoting the growth thereof which comprises an inert carrier and an effective amount of compound of claim 1.

20. A process for the preparation of a compound of claim 1 which comprises preparing the alkali metal salt of the compound having the formula:

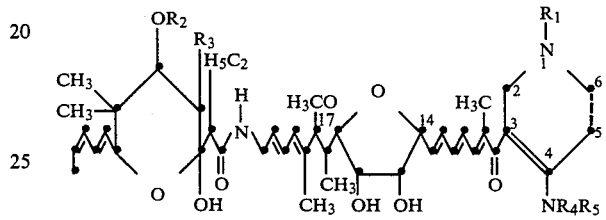

wherein $R_1$, $R_2$, $R_3$ and the broken line are as defined in claim 1; treating the alkali metal salt with a substituted chlorophosphate or dichlorophosphate and reacting the thus prepared phosphate intermediate with ammonia or $NHR_4R_5$ wherein $R_4$ and $R_5$ are as defined in claim 1.

* * * * *